US012035940B2

(12) United States Patent
LaPierre et al.

(10) Patent No.: US 12,035,940 B2
(45) Date of Patent: *Jul. 16, 2024

(54) CENTERING MECHANISMS FOR A SURGICAL ACCESS ASSEMBLY

(71) Applicant: Covidien LP, Mansfield, MA (US)

(72) Inventors: Nicolette LaPierre, Windsor Locks, CT (US); Jacob Baril, Norwalk, CT (US); Matthew Dinino, Newington, CT (US); Justin Thomas, New Haven, CT (US); Saumya Banerjee, Southington, CT (US); Roy Pilletere, Middletown, CT (US)

(73) Assignee: Covidien LP, Mansfield, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/902,046

(22) Filed: Sep. 2, 2022

(65) Prior Publication Data
US 2022/0401127 A1 Dec. 22, 2022

Related U.S. Application Data

(63) Continuation of application No. 16/564,534, filed on Sep. 9, 2019, now Pat. No. 11,432,843.

(51) Int. Cl.
*A61B 7/00* (2006.01)
*A61B 17/00* (2006.01)
(Continued)

(52) U.S. Cl.
CPC ...... *A61B 17/3423* (2013.01); *A61B 17/0057* (2013.01); *A61B 17/3474* (2013.01);
(Continued)

(58) Field of Classification Search
CPC .................................................. A61B 17/3423
See application file for complete search history.

(56) References Cited

U.S. PATENT DOCUMENTS

| 3,402,710 A | 9/1968 | Paleschuck |
| 3,495,586 A | 2/1970 | Regenbogen |

(Continued)

FOREIGN PATENT DOCUMENTS

| CA | 2702419 A1 | 11/2010 |
| EP | 0226026 A2 | 6/1987 |

(Continued)

OTHER PUBLICATIONS

U.S. Appl. No. 16/394,043, filed Apr. 25, 2019, inventor Lorenzo Vaccarella.

(Continued)

*Primary Examiner* — Christian A Sevilla
(74) *Attorney, Agent, or Firm* — Carter, DeLuca & Farrell LLP

(57) ABSTRACT

An access assembly includes an instrument valve housing defining a cavity, and a valve assembly. The valve assembly includes a flange seal member, a seal assembly, a centering mechanism, and a retainer frame assembly. The flange seal member includes an arcuate portion configured to adjustably engage first and second surfaces of the instrument valve housing in a sealing relation. The centering mechanism is configured to bias the valve assembly towards a generally centered position within the cavity. The centering mechanism includes a plurality of coils including inner coil portions operatively secured with the seal assembly, and outer coil portions configured to engage the first surface of the instrument valve housing. The retainer frame assembly includes first and second members. The inner coil portion of the centering mechanism is disposed between seal assembly and the second member of the retainer frame assembly.

20 Claims, 9 Drawing Sheets

(51) Int. Cl.
*A61B 17/34* (2006.01)
*A61B 17/02* (2006.01)
(52) U.S. Cl.
CPC .............. *A61B 17/3498* (2013.01); *A61B 2017/00637* (2013.01); *A61B 17/0218* (2013.01); *A61B 2017/3419* (2013.01); *A61B 2017/3445* (2013.01)

(56) References Cited

U.S. PATENT DOCUMENTS

| | | | |
|---|---|---|---|
| 4,016,884 A | 4/1977 | Kwan-Gett | |
| 4,112,932 A | 9/1978 | Chiulli | |
| 4,183,357 A | 1/1980 | Bentley et al. | |
| 4,356,826 A | 11/1982 | Kubota | |
| 4,402,683 A | 9/1983 | Kopman | |
| 4,653,476 A | 3/1987 | Bonnet | |
| 4,737,148 A | 4/1988 | Blake | |
| 4,863,430 A | 9/1989 | Klyce et al. | |
| 4,863,438 A | 9/1989 | Gauderer et al. | |
| 4,984,564 A | 1/1991 | Yuen | |
| 5,002,557 A | 3/1991 | Hasson | |
| 5,073,169 A | 12/1991 | Raiken | |
| 5,082,005 A | 1/1992 | Kaldany | |
| 5,122,122 A | 6/1992 | Allgood | |
| 5,159,921 A | 11/1992 | Hoover | |
| 5,176,697 A | 1/1993 | Hasson | |
| 5,183,471 A | 2/1993 | Wilk | |
| 5,192,301 A | 3/1993 | Kamiya et al. | |
| 5,209,741 A | 5/1993 | Spaeth | |
| 5,209,754 A | 5/1993 | Ahluwalia | |
| 5,217,466 A | 6/1993 | Hasson | |
| 5,226,426 A * | 7/1993 | Yoon | A61B 10/0266 604/164.01 |
| 5,242,409 A | 9/1993 | Buelna | |
| 5,242,415 A | 9/1993 | Kantrowitz et al. | |
| 5,257,973 A | 11/1993 | Villasuso | |
| 5,257,975 A | 11/1993 | Foshee | |
| 5,269,772 A | 12/1993 | Wilk | |
| 5,290,249 A | 3/1994 | Foster et al. | |
| 5,312,391 A | 5/1994 | Wilk | |
| 5,312,417 A | 5/1994 | Wilk | |
| 5,314,417 A | 5/1994 | Stephens et al. | |
| 5,318,516 A | 6/1994 | Cosmescu | |
| 5,330,486 A | 7/1994 | Wilk | |
| 5,334,143 A | 8/1994 | Carroll | |
| 5,336,169 A | 8/1994 | Divilio et al. | |
| 5,336,203 A | 8/1994 | Goldhardt et al. | |
| 5,337,937 A | 8/1994 | Remiszewski et al. | |
| 5,345,927 A | 9/1994 | Bonutti | |
| 5,360,417 A | 11/1994 | Gravener et al. | |
| 5,364,372 A * | 11/1994 | Danks | A61B 17/3462 604/164.12 |
| 5,366,478 A | 11/1994 | Brinkerhoff et al. | |
| 5,375,588 A | 12/1994 | Yoon | |
| 5,378,588 A | 1/1995 | Tsuchiya | |
| 5,391,156 A | 2/1995 | Hildwein et al. | |
| 5,394,863 A | 3/1995 | Sanford et al. | |
| 5,395,367 A | 3/1995 | Wilk | |
| 5,437,683 A | 8/1995 | Neumann et al. | |
| 5,445,615 A | 8/1995 | Yoon | |
| 5,451,222 A | 9/1995 | De Maagd et al. | |
| 5,460,170 A | 10/1995 | Hammerslag | |
| 5,464,409 A | 11/1995 | Mohajer | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,520,698 A | 5/1996 | Koh | |
| 5,522,791 A | 6/1996 | Leyva | |
| 5,524,644 A | 6/1996 | Crook | |
| 5,540,648 A | 7/1996 | Yoon | |
| 5,545,150 A | 8/1996 | Danks et al. | |
| 5,545,179 A | 8/1996 | Williamson, IV | |
| 5,556,385 A | 9/1996 | Andersen | |
| 5,569,159 A | 10/1996 | Anderson et al. | |
| 5,577,993 A | 11/1996 | Zhu et al. | |
| 5,584,850 A * | 12/1996 | Hart | A61B 17/3498 604/278 |
| 5,601,581 A | 2/1997 | Fogarty et al. | |
| 5,624,399 A | 4/1997 | Ackerman | |
| 5,634,911 A | 6/1997 | Hermann et al. | |
| 5,634,937 A | 6/1997 | Mollenauer et al. | |
| 5,643,285 A | 7/1997 | Rowden et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,656,013 A | 8/1997 | Yoon | |
| 5,672,168 A | 9/1997 | de la Torre et al. | |
| 5,683,378 A | 11/1997 | Christy | |
| 5,685,857 A | 11/1997 | Negus et al. | |
| 5,697,946 A | 12/1997 | Hopper et al. | |
| 5,709,675 A | 1/1998 | Williams | |
| 5,713,858 A | 2/1998 | Heruth et al. | |
| 5,713,869 A | 2/1998 | Morejon | |
| 5,722,962 A | 3/1998 | Garcia | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,752,970 A | 5/1998 | Yoon | |
| 5,782,817 A | 7/1998 | Franzel et al. | |
| 5,795,290 A | 8/1998 | Bridges | |
| 5,803,921 A | 9/1998 | Bonadio | |
| 5,810,712 A | 9/1998 | Dunn | |
| 5,813,409 A | 9/1998 | Leahy et al. | |
| 5,830,191 A | 11/1998 | Hildwein et al. | |
| 5,836,871 A | 11/1998 | Wallace et al. | |
| 5,836,913 A | 11/1998 | Orth et al. | |
| 5,840,077 A | 11/1998 | Rowden et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,865,817 A | 2/1999 | Moenning et al. | |
| 5,871,474 A | 2/1999 | Hermann et al. | |
| 5,876,413 A | 3/1999 | Fogarty et al. | |
| 5,894,843 A | 4/1999 | Benetti et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,914,415 A | 6/1999 | Tago | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,976,174 A | 11/1999 | Ruiz | |
| 5,997,515 A | 12/1999 | de la Torre et al. | |
| 6,017,355 A | 1/2000 | Hessel et al. | |
| 6,018,094 A | 1/2000 | Fox | |
| 6,024,736 A | 2/2000 | de la Torre et al. | |
| 6,030,402 A | 2/2000 | Thompson et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,059,816 A | 5/2000 | Moenning | |
| 6,068,639 A | 5/2000 | Fogarty et al. | |
| 6,077,288 A * | 6/2000 | Shimomura | A61B 17/3462 606/186 |
| 6,086,603 A | 7/2000 | Termin et al. | |
| 6,099,506 A | 8/2000 | Macoviak et al. | |
| 6,110,154 A | 8/2000 | Shimomura et al. | |
| 6,142,936 A | 11/2000 | Beane et al. | |
| 6,156,006 A | 12/2000 | Brosens et al. | |
| 6,162,196 A * | 12/2000 | Hart | A61B 17/3462 604/167.03 |
| 6,171,282 B1 | 1/2001 | Ragsdale | |
| 6,197,002 B1 | 3/2001 | Peterson | |
| 6,217,555 B1 | 4/2001 | Hart et al. | |

(56) References Cited

U.S. PATENT DOCUMENTS

| | | |
|---|---|---|
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |

(56) References Cited

U.S. PATENT DOCUMENTS

| | | |
|---|---|---|
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 11,432,843 B2 | 9/2022 | Lapierre et al. |
| 2001/0037053 A1 | 11/2001 | Bonadio et al. |
| 2002/0013542 A1* | 1/2002 | Bonadio ............ A61M 25/0119 |
| | | 601/134 |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0064100 A1* | 4/2004 | Smith ................ A61B 17/3462 |
| | | 606/167 |
| 2004/0068232 A1* | 4/2004 | Hart ................... A61B 17/3498 |
| | | 606/167 |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0059934 A1* | 3/2005 | Wenchell ........... A61B 18/1445 |
| | | 604/167.01 |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |

(56) References Cited

U.S. PATENT DOCUMENTS

| | | | |
|---|---|---|---|
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0025477 A1 * | 1/2015 | Evans ............... A61M 39/06 604/256 |
| 2015/0031958 A1 | 1/2015 | Kleyman |
| 2019/0105076 A1 | 4/2019 | Harris et al. |

FOREIGN PATENT DOCUMENTS

| | | | |
|---|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 1994896 A1 * | 11/2008 | ......... A61B 17/3462 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 2432408 A2 | 3/2012 |
| EP | 2664290 A1 | 11/2013 |
| GB | 2469083 | 4/2009 |
| JP | 2001128985 A | 5/2001 |
| JP | 2015535712 A | 12/2015 |
| JP | 2017508534 A | 3/2017 |
| JP | 2019037770 A | 3/2019 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 A1 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |

OTHER PUBLICATIONS

U.S. Appl. No. 16/238,823, filed Jan. 3, 2019, inventor Garrett Ebersole.
Extended European Search Report issued in EP Application No. 20194861.9, dated Feb. 4, 2021.
Japanese Office Action dated May 1, 2024, issued in corresponding Japanese Application No. 2020132848, 3 pages.

* cited by examiner

CENTERING MECHANISMS FOR A SURGICAL ACCESS ASSEMBLY

CROSS-REFERENCE TO RELATED APPLICATION

This application is a continuation of U.S. patent application Ser. No. 16/564,534, filed on Sep. 9, 2019, now U.S. Pat. No. 11,432,843, the content of which is hereby incorporated by reference in its entirety.

FIELD

The present disclosure relates to surgical access assemblies for minimally invasive surgery. More particularly, the present disclosure relates to centering mechanisms for use with the surgical access assemblies.

BACKGROUND

In order to facilitate minimally invasive surgery, a working space must be created in the desired surgical space. An insufflation gas, typically $CO_2$, is introduced into the abdomen of the patient to create an inflated state called pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals. Typically, a "zero-seal" in the surgical access assemblies seals a surgical access assembly in the absence of a surgical instrument therein, and an instrument seal seals around a surgical instrument that is inserted through the surgical access assembly.

Surgical procedures require a robust seal capable of adjusting to manipulation of surgical instrumentation extending through the surgical access assemblies without compromising seal integrity. Therefore, it would be beneficial to have a surgical access assembly with improved seal capability and durability.

SUMMARY

In accordance with an embodiment of the present disclosure, an access assembly includes an instrument valve housing defining a cavity, and a valve assembly disposed within the cavity of the instrument valve housing. The valve assembly includes a flange seal member, a seal assembly, a centering mechanism, and a retainer frame assembly. The flange seal member includes an arcuate portion configured to adjustably engage first and second surfaces of the instrument valve housing in a sealing relation. The seal assembly is configured to engage a surgical instrument inserted into the access assembly in a sealing relation. The centering mechanism is configured to bias the valve assembly towards a generally centered position within the cavity of the instrument valve housing. The centering mechanism includes a plurality of coils arranged in a circular configuration and defines a central opening. The plurality of coils includes inner coil portions operatively secured with the seal assembly, and outer coil portions configured to engage the first surface of the instrument valve housing. The retainer frame assembly is configured to couple the centering mechanism, the flange seal member, and the seal assembly as a single construct. The retainer frame assembly includes first and second members. The inner coil portion of the centering mechanism is disposed between seal assembly and the second member of the retainer frame assembly.

In an embodiment, the centering mechanism may have a substantially flat profile.

In another embodiment, the centering mechanism may be formed of a resilient material to transition the centering mechanism between a first state, in which, the central opening of the centering mechanism is disposed in a generally centered position, and a second state, in which, the central opening is radially displaced from the generally centered position.

In yet another embodiment, portions of the centering mechanism may be compressible when the centering mechanism is in the second state.

In an embodiment, each coil of the plurality of coils of the centering mechanism may have a circular profile.

In another embodiment, each coil may extend between the first surface of the instrument valve housing and a gap defined by a pair of adjacent pins of the first member of the retainer frame assembly.

In yet another embodiment, adjacent inner coil portions may define a gap therebetween.

In an embodiment, the first member of the retainer frame assembly may include a plurality of pins, and the second member of the retainer frame assembly may define an annular groove configured to receive the plurality of pins.

In another embodiment, each pin of the plurality of pins of the first member may be at least partially disposed in the gap defined between the adjacent inner coil portions such that at least a portion of each inner coil portion is secured between adjacent pins.

In an embodiment, the outer coil portions of the centering mechanism may be radially outward of the second member of the retainer frame assembly.

In another embodiment, the seal assembly may include a plurality of radial protrusions peripherally arranged about a central opening of the seal assembly. Each radial protrusion of the plurality of radial protrusions may be configured to support a corresponding inner coil portion of the centering mechanism.

In yet another embodiment, the valve assembly may further include a guard assembly configured to be secured with the flange seal member. The guard assembly may be configured to protect the seal assembly during insertion and manipulation of a surgical instrument.

In still yet another embodiment, the flange seal member may include opposing first and second surfaces. The guard assembly may be disposed on the first surface of the flange seal member in a superposed relation, and the seal assembly may be detachably secured with the second surface of the flange seal member.

In accordance with another embodiment of the present disclosure, an access assembly includes an instrument valve housing defining a cavity, and a valve assembly disposed within the cavity of the instrument valve housing. The valve assembly includes a flange seal member, a seal assembly, and a centering mechanism. The flange seal member includes an arcuate portion configured to adjustably engage lateral and distal surfaces of the instrument valve housing in a sealing relation. The seal assembly is configured to engage a surgical instrument inserted into the access assembly in a sealing relation. The centering mechanism is configured to bias the valve assembly towards a generally centered position within the cavity of the instrument valve housing. The centering mechanism includes a mesh having a toroidal shape. The mesh is configured to be interposed between the lateral surface of the instrument valve housing and a portion of the flange seal member.

In an embodiment, the mesh may be disposed distally of the arcuate portion of the flange seal member.

In another embodiment, the mesh may be transitionable between a first state, in which, a central opening defined by the mesh is in a generally centered position, and a second state, in which, the central opening of the mesh is radially displaced.

In an embodiment, the valve assembly may include a retainer frame assembly including first and second members. The retainer frame assembly may be configured to couple the flange mechanism, the flange seal member, and the seal assembly as a single construct.

In another embodiment, the central opening of the mesh may be concentrically disposed with a central opening defined by the seal assembly.

In an embodiment, a portion of the arcuate portion of the flange seal member may be in superposed relation with the mesh.

In another embodiment, the mesh may be radially compressible such that a portion of the arcuate portion of the flange seal member engages the lateral surface of the instrument valve housing when at least a portion of the mesh is compressed.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
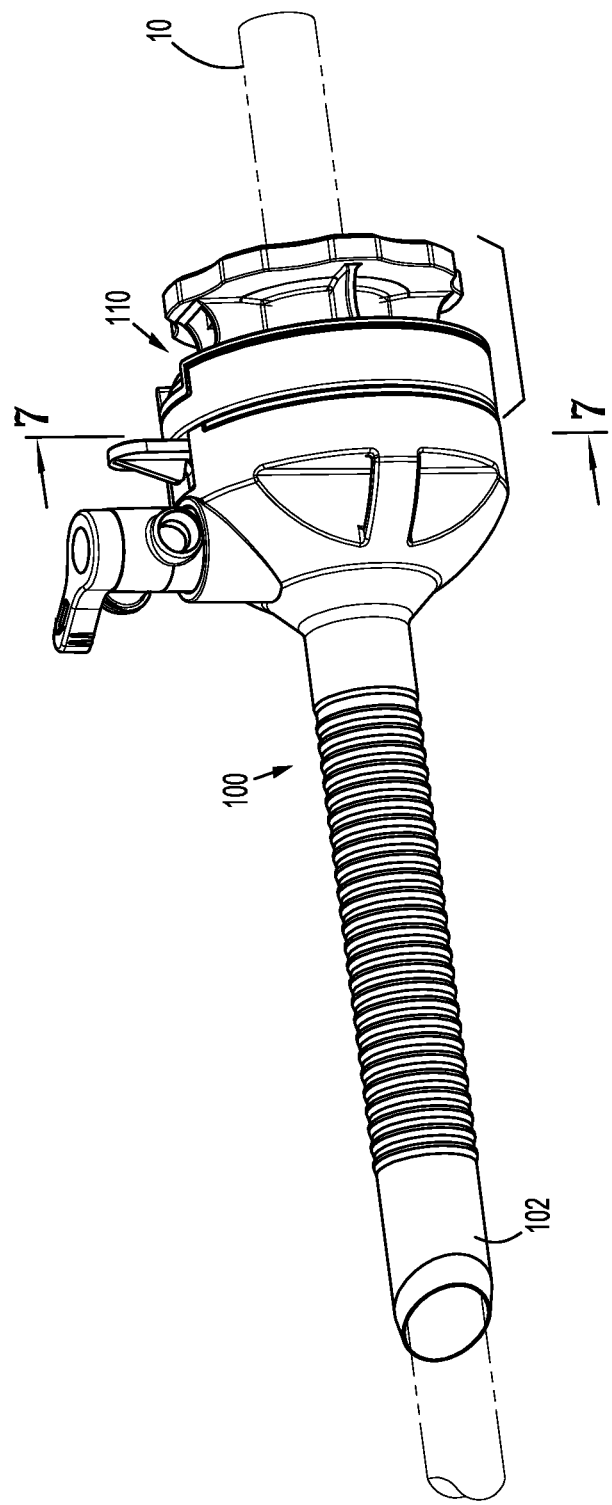
FIG. 1 is a perspective view of a surgical access assembly in accordance with an embodiment of the present disclosure.

Particular embodiments of the present disclosure are described hereinbelow with reference to the accompanying drawings; however, it is to be understood that the disclosed embodiments are merely exemplary of the specific disclosure and may be embodied in various forms. Well-known functions or constructions are not described in detail to avoid obscuring the present disclosure in unnecessary detail. Therefore, structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments.

Figure 2:
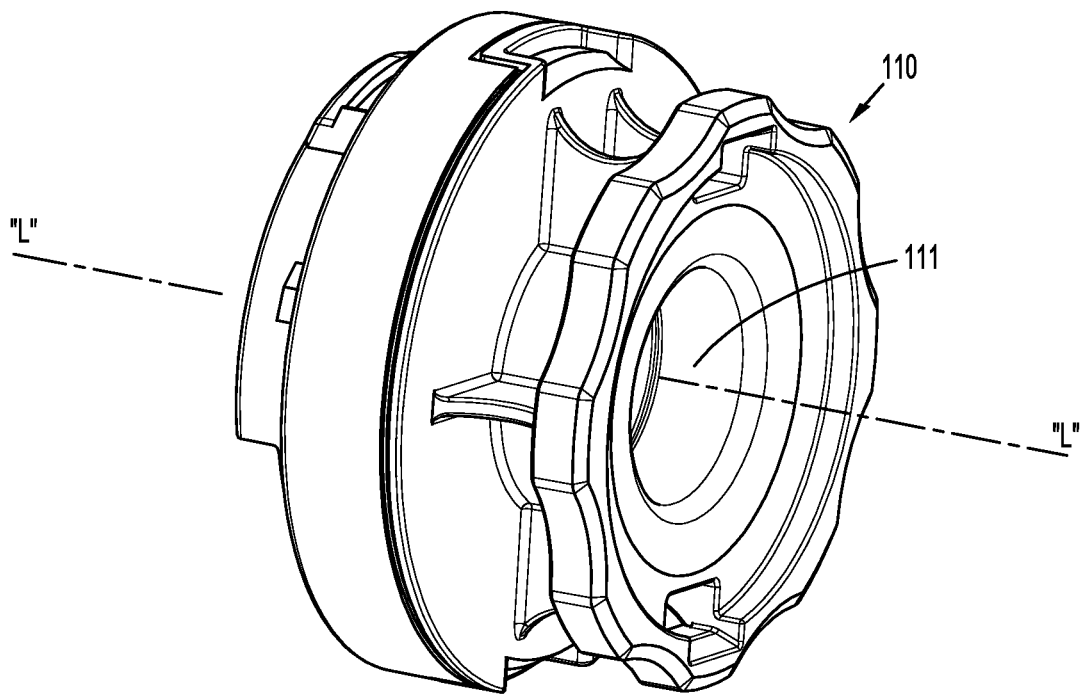
FIG. 2 is a perspective view of an instrument valve housing of the surgical access assembly of FIG. 1.
Figure 3:
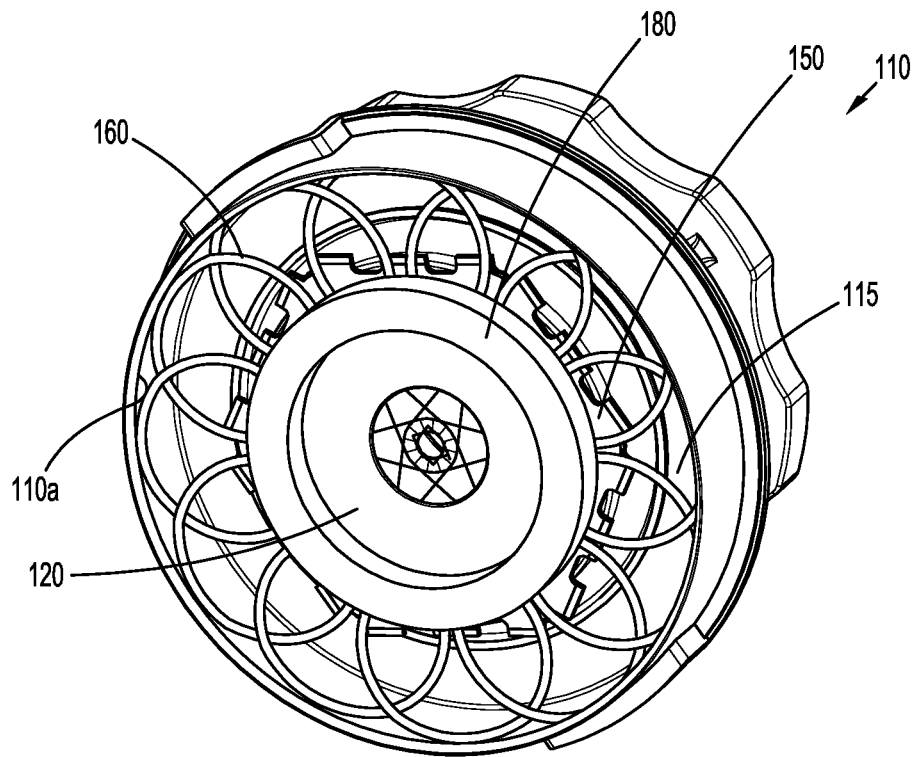
FIG. 3 is a bottom perspective view of the instrument valve housing of FIG. 2.

With initial reference now to FIGS. 1-3, a surgical access assembly according to aspects of the present disclosure is shown generally as a cannula assembly 100. The cannula assembly 100 may be utilized during minimally invasive surgery, e.g., laparoscopic surgery, and provide for the sealed access of surgical instruments into an insufflated body cavity, such as the abdominal cavity. The cannula assembly 100 includes a cannula 102 and an instrument valve housing 110 detachably secured to the cannula 102. The instrument valve housing 110 defines a longitudinal passage 111 for receipt of a surgical instrument 10. In addition, the instrument valve housing 110 defines a cavity 115 configured to adjustably support a valve assembly 120 therein. The valve assembly 120 is supported within the instrument valve housing 110 to provide sealed passage of the surgical instrument 10 through the cannula assembly 100. In embodiments, the instrument valve housing 110 may include, e.g., knurls, indentations, tabs, or be otherwise configured to facilitate engagement by a clinician.

The cannula assembly 100 may be configured for use with an obturator (not shown) inserted through the instrument valve housing 110 and the cannula 102. The obturator may have a blunt distal end, or a bladed or non-bladed penetrating distal end. The obturator may be used to incise the abdominal wall so that the cannula assembly 100 may be introduced into the abdomen. The handle of the obturator may engage or selectively lock into the instrument valve housing 110 of the cannula assembly 100. For a detailed description of the structure and function of exemplary obturators and cannulas, reference may be made to commonly owned International Patent Publication No. WO 2016/186905 ("the '905 publication"), the entire disclosure of which is hereby incorporated by reference herein.

In addition, the cannula assembly 100 may also include features for securement with a patient. For example, a distal end of the cannula 102 may support a balloon anchor or another expandable member that engages the abdomen from the interior side. A feature on the opposite side of the abdominal wall may be used to further stabilize the cannula assembly 100, such as adhesive tabs or adjustable foam collars. For a detailed description of such features on a cannula assembly, reference may be made to commonly owned U.S. Pat. No. 7,300,448 ("the '448 Patent"), the entire disclosure of which is hereby incorporated by reference herein.

Figure 5:
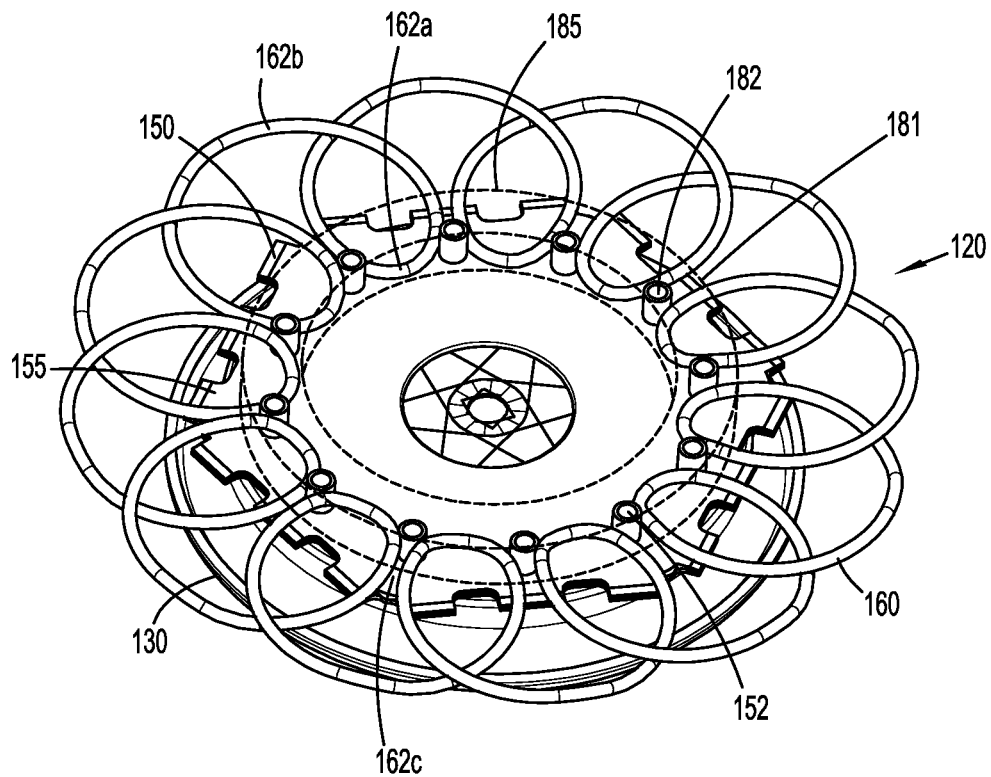
FIG. 5 is a bottom perspective view of the valve assembly of FIG. 4.
Figure 4:
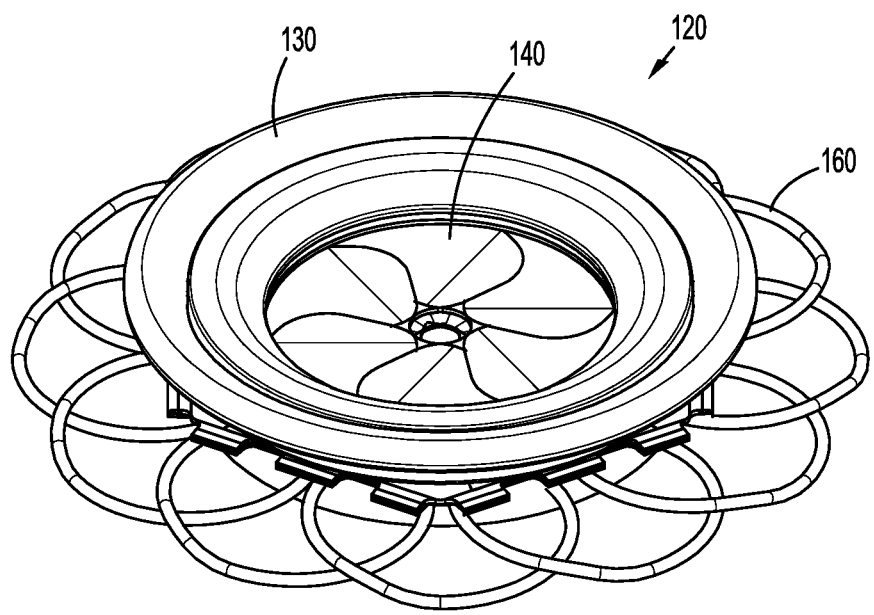
FIG. 4. is a top perspective view of a valve assembly of the instrument valve housing of FIG. 2 in accordance with an embodiment of the present disclosure.
Figure 6:
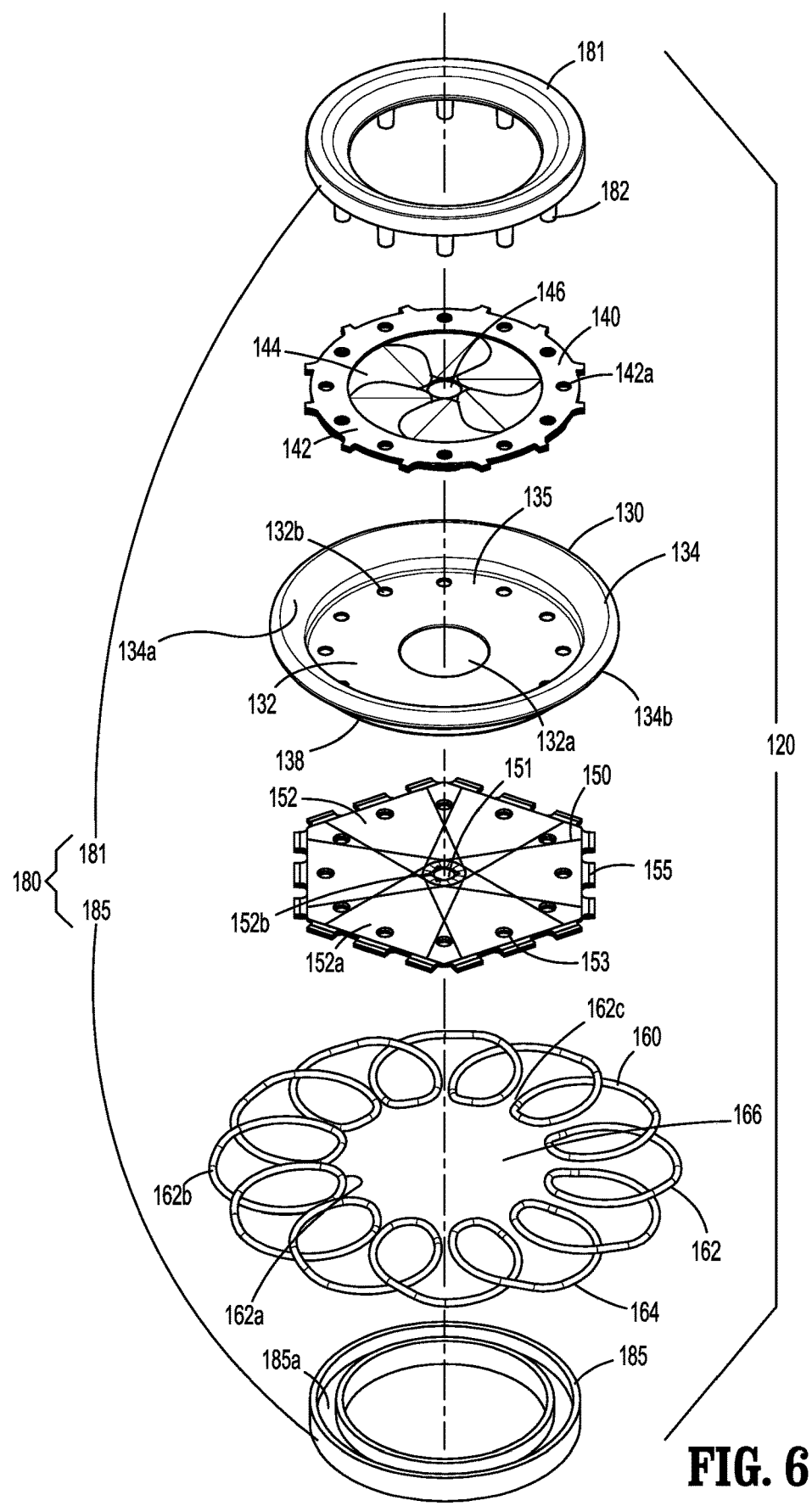
FIG. 6 is an exploded perspective view of the valve assembly of FIG. 4 with parts separated.

With reference now to FIGS. 4-6, the valve assembly 120 in accordance with an embodiment of the present disclosure includes a flange seal member 130, a guard assembly 140, a seal assembly 150, a centering mechanism 160, and a retainer frame assembly 180. The flange seal member 130 includes an annular base 132 and a flange portion 138 extending from the annular base 132 such that the flange seal member 130 defines a recess 135 configured to receive the guard assembly 140 therein. The annular base 132 defines a central opening 132a configured to receive the surgical instrument 10 therethrough, and a plurality of bores 132b circumferentially defined about the central opening 132a. The plurality of bores 132b is configured to receive respective pins 182 of a first member 181 of the retainer frame assembly 180, as will be discussed below.

In particular, the flange portion 138 of the flange seal member 130 includes an arcuate portion 134 extending radially outward. The arcuate portion 134 includes inner and outer segments 134a, 134b defining a gap (not shown) therebetween. Under such a configuration, the arcuate portion 134 is configured to adjustably engage a first surface such as, e.g., a distal surface (not shown), of the instrument valve housing 110 in a sealing relation and maintain such contact during insertion and movement of the surgical instrument 10 in the longitudinal passage 111 (FIG. 2). For example, the distal surface of the instrument valve housing 110 may be orthogonal to a longitudinal axis "L-L" (FIG. 2) defined by the longitudinal passage 111 of the instrument valve housing 110. A conventional base seal member may suffer from buckling or bending during movement thereof, which may result in a loss of sealing contact with the surgical instrument 10 and/or the instrument valve housing. In contrast, the flange seal member 130 engages the instrument valve housing 110 in a sealing relation during movement of the valve assembly 120 within the cavity 115. In particular, the arcuate portion 134 of the flange seal member 130 adjustably engages the distal surface of the instrument valve housing 110 to enable sealing contact during, e.g., radial, movement in the cavity 115.

In addition, the arcuate portion 134 of the flange seal member 130 is configured to adjustably engage a second surface such as, e.g., a lateral surface 110a (FIG. 3), of the instrument valve housing 110 in a sealing relation during an off-centered movement of the seal assembly 120. The lateral surface 110a may be substantially parallel to the longitudinal axis "L-L" (FIG. 2) defined by the longitudinal passage 111 (FIG. 2) of the instrument valve housing 110. Under such a configuration, the arcuate portion 134 may sealingly engage two surfaces that are substantially orthogonal to each other. In particular, the gap defined between the inner and outer segments 134a, 134b of the arcuate portion 134 of the flange seal member 130 enables the arcuate portion 134 to adjustably engage the lateral surface 110a, as well as the distal surface (not shown), of the instrument valve housing 110 in a sealing relation during movement of the valve assembly 120. Specifically, when a portion of the centering mechanism 160 is compressed against the lateral surface 110a of the instrument valve housing 110, the outer segment 134b of the arcuate portion of the flange seal member 130 may deflect radially inward to maintain sealing contact with the instrument valve housing 110. Under such a configuration, the flange seal member 130 may engage the instrument valve assembly 110 at multiple locations and enhance sealing relation with the instrument valve assembly 110. In this manner, the flange seal member 130 is configured to engage at least two surfaces of the instrument valve housing 110 in a sealing relation when the centering mechanism 160 is radially off-center, as will be discussed below.

With particular reference to FIG. 6, the guard assembly 140 is configured to be disposed in the recess 135 defined in the flange seal member 130, in a superposed relation with the annular base 132. The guard assembly 140 is configured to protect the seal assembly 150 during insertion and withdrawal of the surgical instrument 10 into and from the seal assembly 150. The guard assembly 140 includes an annular member 142 and a plurality of petals 144 circumferentially supported on the annular member 142 such that adjacent petals 144 are at least partially overlapped to enable slidable movement therebetween. The plurality of petals 144 defines a central opening 146. The petals 144 also operate to guide and orient the surgical instrument 10 through the seal assembly 150. The central opening 146 is configured for receipt of the surgical instrument 10 therethrough. The annular member 142 defines a circumferentially arranged bores 142a, and a peripheral portion of each petal 144 defines bores (not shown) in alignment with the respective bores of 142a of the annular member 142 to receive the respective pins 182 of the first member of the retainer frame assembly 180, as will be discussed below.

The guard assembly 140 may be formed from, e.g., a sheet of plastic/polymeric material, by stamping with a tool that forms the petals 144. The petals 144 are configured to flex distally (i.e., away from the first member 181 of the retainer frame assembly 180), upon engagement with the surgical instrument 10 to facilitate passage of the surgical instrument 10 through the seal assembly 150, which, in turn, stretches the seal assembly 150 to increase the size of a central opening 151 of the seal assembly 150. The increased size of the central opening 151 of the seal assembly 150 permits receipt of the surgical instrument 10 (FIG. 7) through the valve assembly 120.

It is envisioned that the guard assembly 140 may include any number of petals 144 and the petals 144 may include flap portions of any size or configuration. For a detailed description of a guard assembly, reference may be made to U.S. Pat. Nos. 5,895,377 and 6,569,120, and International Patent Publication No. WO 91/12838, the entire disclosures of which are all hereby incorporated by reference herein, for exemplary guard assemblies.

With continued reference to FIG. 6, the seal assembly 150 of the valve assembly 120 is configured to provide a seal around an outer surface of the surgical instrument 10 passing through the instrument valve housing 110. The seal assembly 150 includes a plurality of seal segments 152 that are stackable to form a seal having a virtual inner circumferential surface defining the central opening 151 to facilitate sealed passage of the surgical instrument 10 through the seal assembly 150. In embodiments, the central opening 151 may be between about 0.025" and about 0.100" in diameter.

The seal assembly 150 may defines, e.g., a substantially planar, hexagonal member. The hexagonal shape facilitates assembly of the seal assembly 150, allowing for quick placement of the seal segments 152 in relation to each other, and/or by allowing for a quick visual check of the seal assembly 150 to ensure that the seal segments 152 are properly assembled. By forming the central opening 151 out of multiple seal segments 152, i.e., forming a virtual inner circumferential surface, instead of having a continuous solid opening through a single seal member, the likelihood of the seal assembly 150 tearing during insertion, removal, and/or use of a surgical instrument 10 therethrough is greatly reduced. The seal segments 152 of the seal assembly 150 may be formed of an elastic material, e.g., rubber, polyisoprene, or silicone elastomers. In one embodiment, the seal assembly 150 is formed of liquid silicon rubber (LSR). In embodiments, the seal segments 152 may include one or more fabric layers. Each seal segment 152 of the seal assembly 150 may be substantially wing-shaped and configured to partially overlap an adjacent seal segment 152 when the seal assembly 150 is in the assembled or stacked configuration. Each seal segment 152 includes a base portion 152a and a seal portion 152b extending from the base portion 152a. The base portion 152a and the seal portion 152b may be formed of the same or different material. The base portion 152a of the seal segment 152 defines a plurality of openings 153 to facilitate assembly and retention of the seal assembly 150 in the stacked configuration. More particularly, the plurality of openings 153 are configured to receive pins 182 of the first member of the retainer frame assembly 180, for securing the seal segments 152 relative to each other. In particular, the seal portion 152b of each seal segment 152 of the seal assembly 150 may taper radially inwardly to facilitate reception of the surgical instrument 10 through the seal assembly 150, and/or may enhance sealing about the surgical instrument 10.

In the assembled or stacked configuration, the seal assembly 150 includes a substantially planar body having a substantially uniform thickness. It is envisioned that the aspects of the present disclosure may be modified for use with an access assembly having a substantially conical body. Misalignment of any one of the seal segments of the seal assembly 150 may compromise the integrity of the seal assembly 150. The configuration of the seal assembly 150 permits visual inspection of the seal assembly 150 to determine if the seal assembly 150 is assembled properly.

With reference back to FIGS. 4-6, the centering mechanism 160 in accordance with an embodiment of the present disclosure is configured to bias the valve assembly 120 towards a generally centered position, i.e., concentrically positioned within the cavity 115 (FIG. 3), of the instrument valve housing 110. The centering mechanism 160 permits, e.g., radial, movement of the valve assembly 120 relative to the instrument valve housing 110 when the surgical instrument 10 is received through the valve assembly 120 and manipulated by a clinician. The centering mechanism 160 returns the valve assembly 120 to a generally centered position once the surgical instrument 10 is withdrawn from the instrument valve housing 110 or the radial movement ceases. The centering mechanism 160 is configured to engage various points of the instrument valve housing 110 to bias the centering mechanism 160 to a generally centered position.

Dynamic leaks are common when a clinician manipulates, e.g., a 5 mm surgical instrument through a 15 mm port during bariatric procedures. In order to reduce and inhibit such dynamic leaks, the centering mechanism 160 is compressible when the valve assembly 120 is diametrically displaced within the cavity 115 (FIG. 3) of the instrument valve housing 110, and the centering mechanism 160 is also resilient such that when the surgical instrument 10 is removed from the instrument valve housing 110 the centering mechanism 160 returns the valve assembly 120 back to the generally centered position. In this manner, the centering mechanism 160 may reduce occurrence of a dynamic leak during manipulation of the surgical instrument 10 within the longitudinal passage 111.

The centering mechanism 160 has a substantially flat profile having a plurality of coils 162. The plurality of coils 162 includes an annular body 164 defining a central opening 166. The central opening 166 is dimensioned to receive the surgical instrument 10 therethrough. In particular, the central opening 166 is dimensioned to enable the clinician to manipulate the surgical instrument 10 while providing maximum degree of freedom. The plurality of coils 162 defines a plurality of inner coil portions 162a and outer coil portions 162b. With particular reference to FIG. 5, adjacent inner coil portions 162a define a gap 162c therebetween. The gap 162c is dimensioned to at least partially receive a pin 182 (FIG. 4) of the first member 181 of the retainer frame assembly 180. In this manner, each inner coil portion 162a is supported by an adjacent pair of pins 182 of the first member 181 of the retainer frame assembly 180. The outer coil portion 162b is radially outward from the seal assembly 150 and is configured to engage the lateral surface 110a (FIG. 3) of the instrument valve housing 110. The adjacent pair of pins 182 inhibits inward radial displacement of the corresponding inner coil portion 162a, while enabling radial compression of the outer coil portion 162b. In this manner, the centering mechanism 160 is compressible and resilient to bias the off-centered valve assembly 120 towards a generally centered position within the cavity 115 (FIG. 3) of the instrument valve housing 110. Under such a configuration, once the surgical instrument 10 is withdrawn from the valve assembly 120 that is in an off-centered position, the centering mechanism 160 returns the valve assembly 120 to the generally centered position. The centering mechanism has the advantage of omnidirectional, generally constant centering forces being applied to the seal assembly. The design allows for a mechanism that always or nearly always returns the seal assembly to a central position, as the centering mechanism is always centered in its natural state. The centering mechanism can be made from surgically acceptable metals or appropriate plastics. It can also be made from materials that can be re-sterilized for use in a reusable trocar cannula assembly.

With brief reference back to FIG. 6, the retainer frame member 180 of the valve assembly 120 is configured to couple the guard assembly 140, the flange seal member 130, the seal assembly 150, and the centering mechanism 160 together as a single construct to form the valve assembly 120. The retainer frame member 180 includes the first member 181 and a second member 185. The first member 181 includes a plurality of pins 182 extending from a distal surface of the first member 181. The second member 185 defines an annular groove 185a configured to receive the plurality of the pins 182 of the first member 181 to secure first member 181 thereto. For example, the pins 182 may be frictionally received in the annular groove 189a. Alternatively, the pins 182 may be welded, glued, adhered, bonded or otherwise secured to the annular groove 185a of the second member 185 in order to secure the first and second members 181, 185 together.

The plurality of pins 182 of the first member 181 extends through the respective bores 142a of the guard assembly 140 and the bores 132b of the flange seal member 130. The plurality of pins 182 further extends through the plurality of openings 153 of the seal assembly 150 and into the annular groove 185a of the second member 185. Under such a configuration, the guard assembly 140 is received in the recess 135 of the flange seal member 130, and the seal assembly 150 is interposed between the flange seal member 130 and the second member 185 of the retainer frame assembly 180.

With particular reference back to FIGS. 4 and 5, as discussed hereinabove, each pin 182 of the first member 181 is disposed at least partially within the gap 162c defined by a pair of adjacent inner coil portions 162a of the centering mechanism 160. Under such a configuration, each inner coil portion 162a is supported by a pair of adjacent pins 182. In addition, the plurality of pins 182 is received in the annular groove 185a of the second member 185. In this manner, portions of the inner coil portions 162 are secured between the seal assembly 150 and the second member 185 of the retainer frame assembly 180. In order to further enhance securement of the inner coil portion 162a between the seal assembly 150 and the second member 185, the seal assembly 150 may include radial protrusions 155 peripherally arranged about the central opening 151 to support portions of the inner coil portion 162a of the centering mechanism 160. The outer coil portions 162 engage the lateral surface 110a (FIG. 3) of the instrument valve housing 110 and biases the valve assembly 120 towards a generally centered position in the cavity 115 of the instrument valve housing 110.

Figure 7:
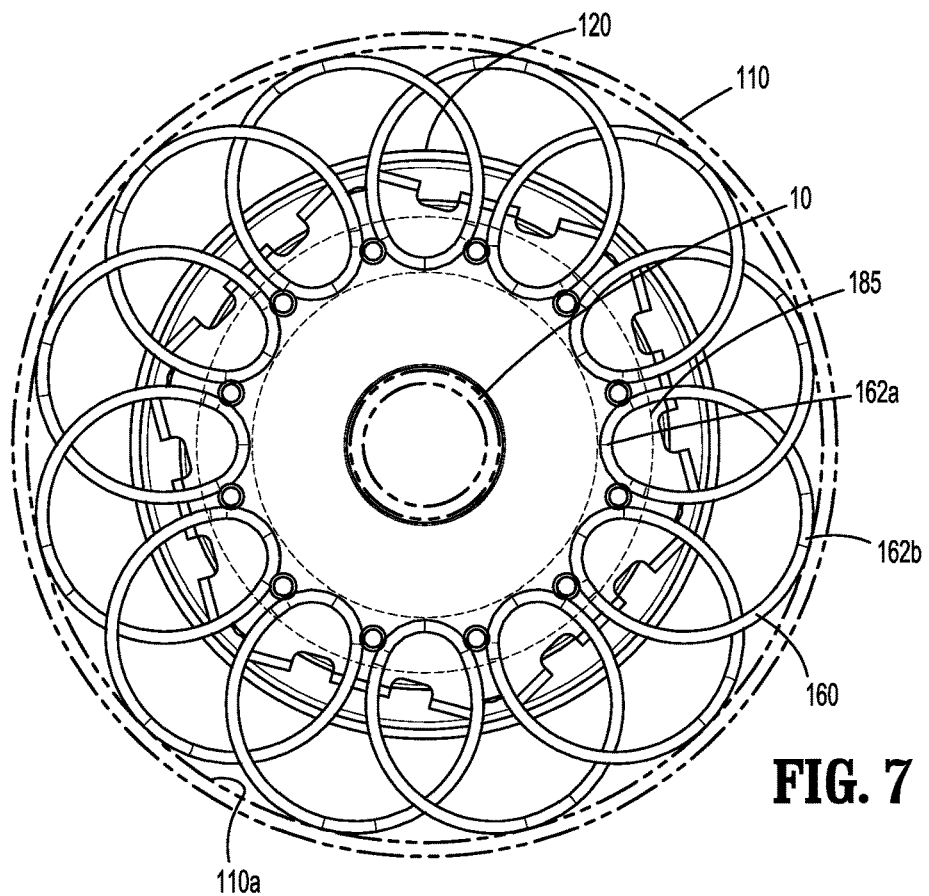
FIG. 7 is a cross-sectional view of the surgical access assembly taken along section line 7-7 of FIG. 1, illustrating the valve assembly in a generally centered position.
Figure 8:
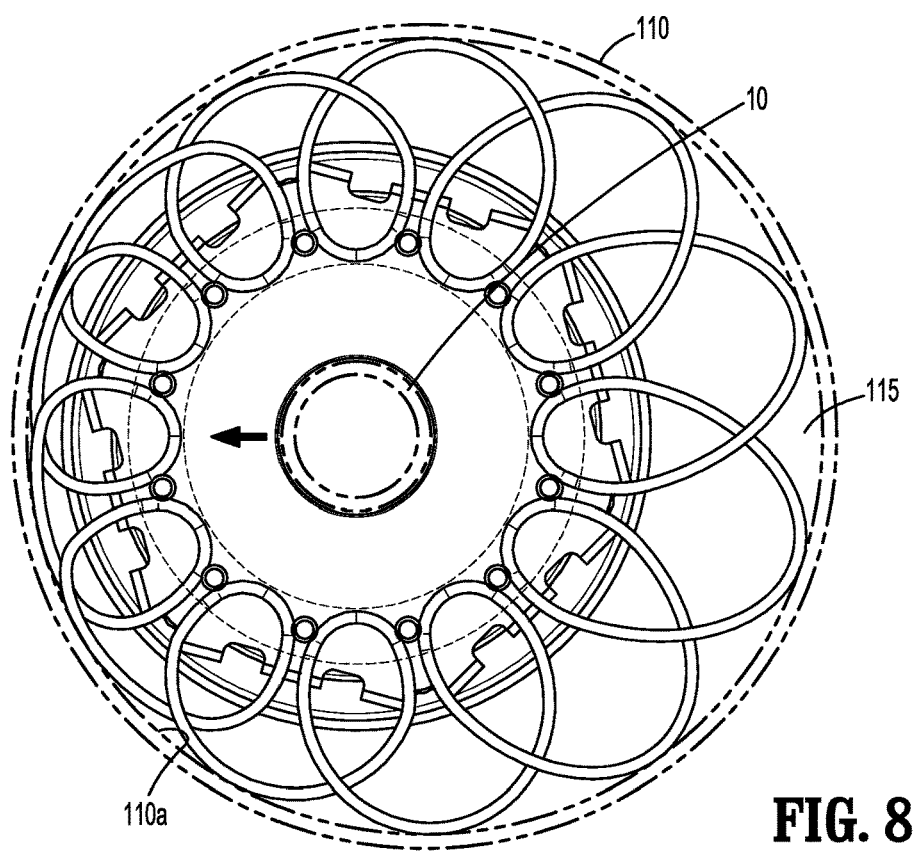
FIG. 8 is a cross-sectional view of the surgical access assembly taken along section line 7-7 of FIG. 1, illustrating the valve assembly in a radially displaced position.

With reference to FIGS. 6-8, in use, the valve assembly 120 is initially positioned generally centered in the instrument valve housing 110 in the absence of the surgical instrument 10. The outer coil portions 162b of the centering mechanism 160 engage the lateral surface 110a of the instrument valve housing 110. At this time, the arcuate portion 134 of the flange seal member 130 engages the distal surface of the instrument valve housing 110 in a sealing relation. As the surgical instrument 10 is introduced into the instrument valve housing 110 through the longitudinal passage 111 (FIG. 2) of the instrument valve housing 110, the distal end of the surgical instrument 10 engages the petals 144 of the guard assembly 140 causing the respective petals 144 to flex distally towards the seal assembly 150. Such flexing of the petals 144 causes the central opening 151 of the seal assembly 150 to open to accommodate passage of the surgical instrument 10. In this manner, the guard assembly 140 protects the seal assembly 150 from tearing or other damage as the surgical instrument 10 is received through and withdrawn from the seal assembly 150.

When the surgical instrument 10 is disposed within the longitudinal passage 111 without any radial forces applied to the surgical instrument 10, the valve assembly 120 may be disposed in a generally centered position as shown in FIG. 7. However, the valve assembly 120 may move within the cavity 115 during a surgical procedure. The clinician may manipulate the surgical instrument 10 such that the valve assembly 120 may be radially displaced, which, in turn, causes some of the outer coil portions 162b of the centering mechanism 160 to be compressed (FIG. 8). At this time, the arcuate portion 134 (FIG. 6) of the flange seal member 130 may engage the lateral surface 110a (FIG. 3), as well as the distal surface, of the instrument valve housing 110 in a sealing relation. Once the surgical instrument 10 is withdrawn from the instrument valve housing 110, the centering mechanism 160 returns the valve assembly 120 to a generally centered position (FIG. 7), while the arcuate portion 134 maintains sealing relation with the distal surface 112a of the upper housing section 112.

Figure 9:
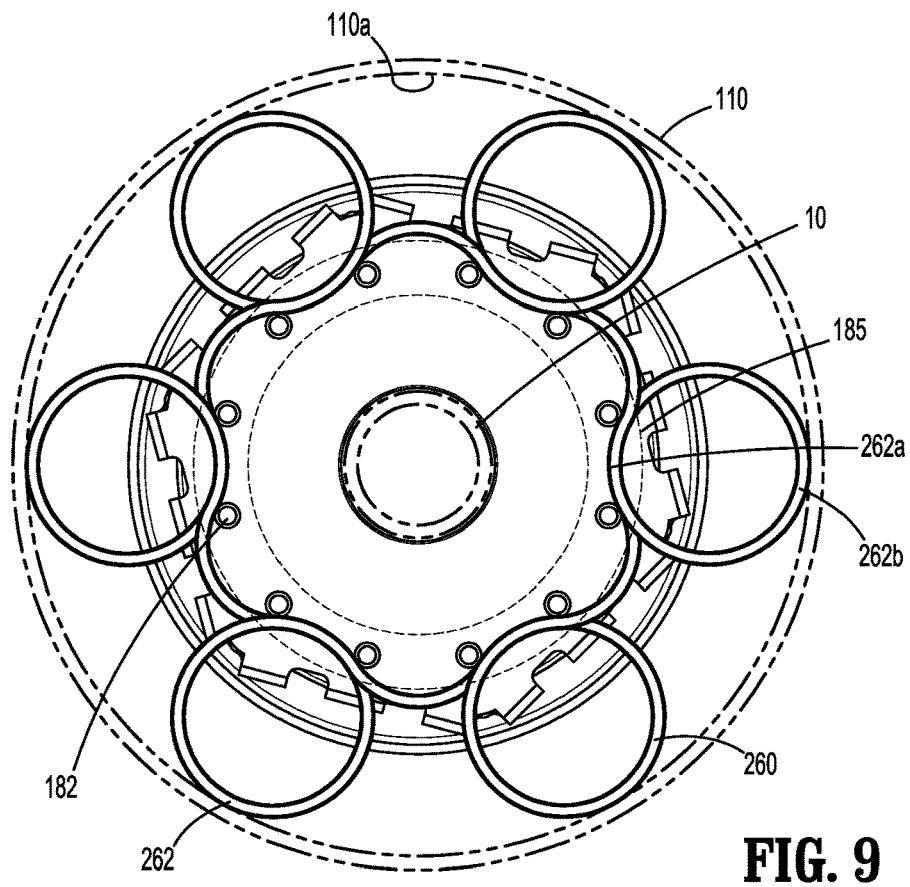
FIG. 9 is a cross-sectional view of a surgical access assembly in accordance with another embodiment of the present disclosure.
Figure 10:
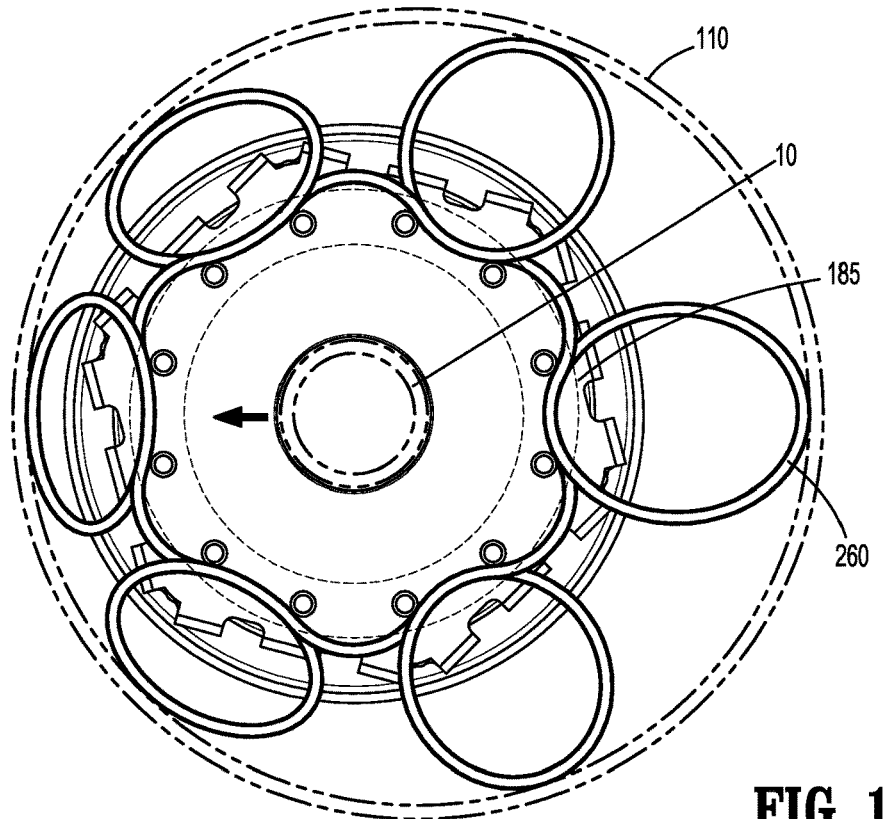
FIG. 10 is a cross-sectional view of the surgical access assembly of FIG. 9, illustrating radial displacement of a valve assembly of FIG. 9.

It is envisioned that the centering mechanism 160 may include coils having different shapes and configurations. With reference to FIGS. 9 and 10, a centering mechanism 260 may include a plurality of coils 262 circumferentially arranged about the centering mechanism 260. In particular, each coil 262 may have a circular profile such that a single circular coil extends between the lateral surface 110a and a gap defined by a pair of adjacent pins 182. As discussed hereinabove, each circular coil 262 may be compressed to, e.g., an oblong shape, during manipulation of the surgical instrument 10 by the clinician, and may spring back to the circular shape when the valve assembly 120 returns to the generally centered position.

Figure 11:
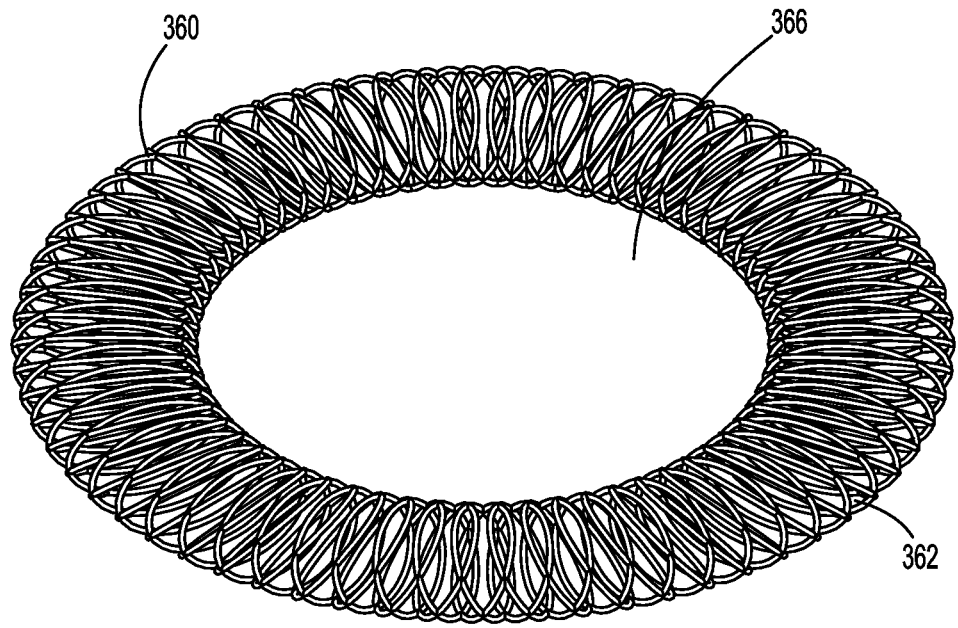
FIG. 11 is a perspective view of a centering mechanism of a valve assembly for use with the surgical access assembly of FIG. 1 in accordance with another embodiment of a present disclosure.
Figure 12:
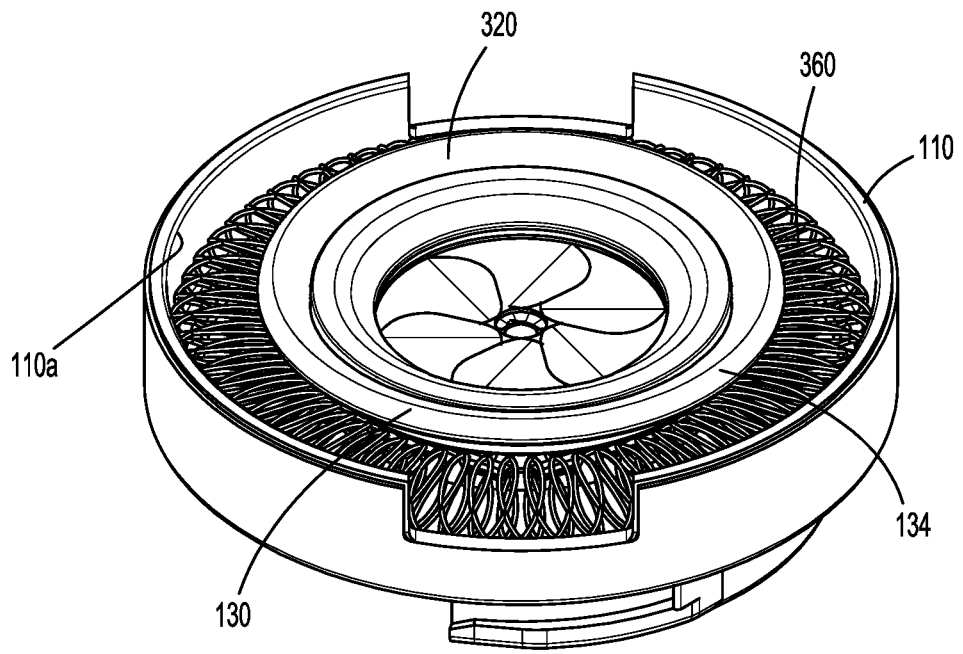
FIG. 12 is a perspective view of an instrument valve housing including the centering mechanism of FIG. 11 with portions of the housing removed.
Figure 13:
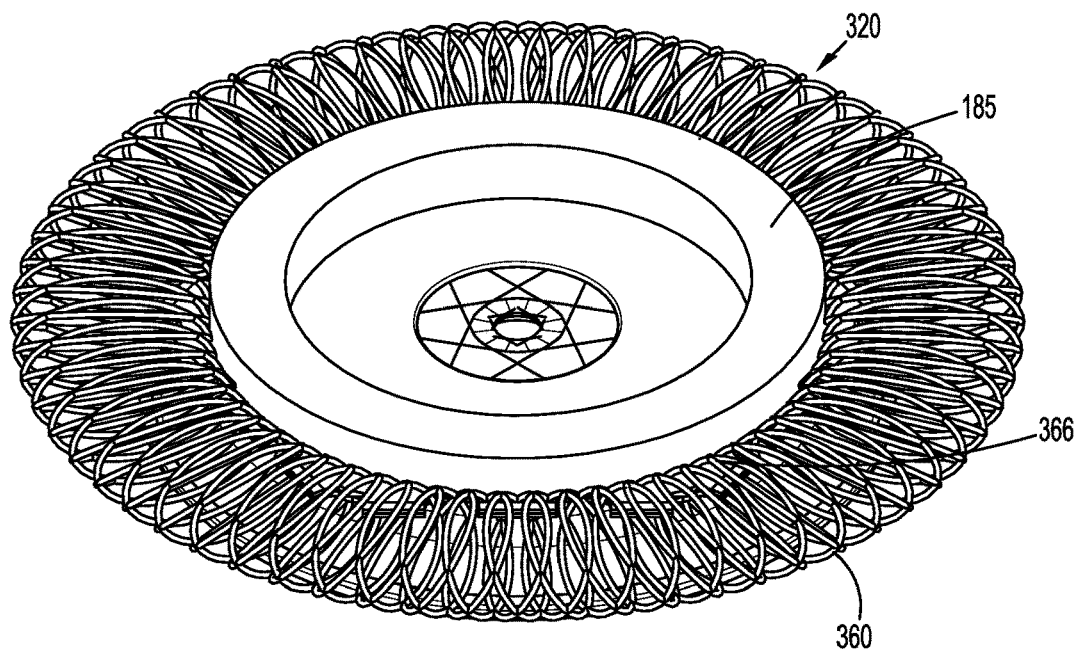
FIG. 13 is a perspective view of a valve assembly of the instrument valve housing of FIG. 12.

With reference now to FIGS. 11 and 12, a centering mechanism in accordance with another embodiment of the present disclosure is generally shown as a centering mechanism 360. The centering mechanism 360 is configured for use with the valve assembly 120 (FIG. 6). Portions of the centering mechanism 360 substantially identical to the centering mechanisms 160, 260 will not be described herein to avoid obscuring the present disclosure in unnecessary detail. The centering mechanism 360 may have, e.g., a toroidal or donut shape, including a mesh or a plurality of coils 362. In particular, the centering mechanism 360 is dimensioned to be in the cavity 115 of the instrument valve housing 110. The centering mechanism 360 is disposed distal of the arcuate portion 134 (FIG. 6) of the flange seal member 130. Moreover, the centering mechanism 360 is configured to engage the lateral surface 110a of the instrument valve housing 110 when the valve assembly 320 is in a generally centered position. Under such a configuration, when the valve assembly 320 is radially displaced, portions of the centering mechanism 360 are compressed during manipulation of a surgical instrument extending through the valve assembly 320. At this time, the arcuate portion 134 of the of the flange seal member 130 may engage the lateral surface 110a of the instrument valve housing 110 in a sealing relation. With reference to FIG. 13, the centering mechanism 360 defines a central opening 366 dimensioned to receive the second member 185 of the retainer frame assembly 180 such that the centering mechanism 360 is interposed between the lateral surface 110a and the second member 185 in an uncompressed state, i.e., when the valve assembly 320 is in a normally biased or a generally centered position.

Figure 14:
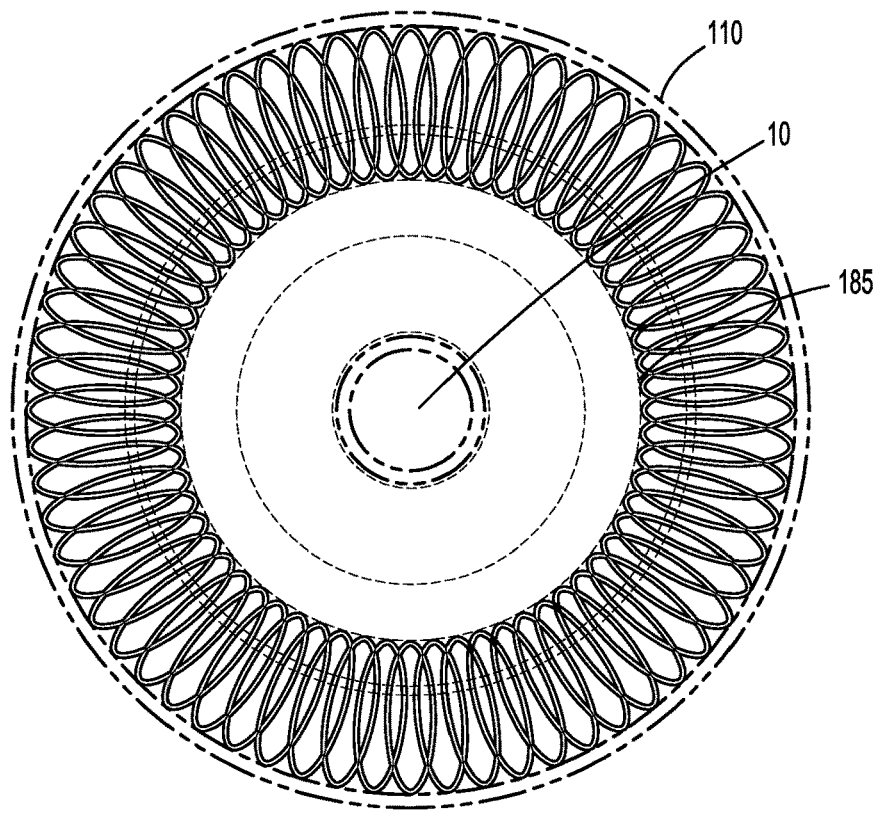
FIG. 14 is a cross-sectional view of the valve housing of FIG. 12.
Figure 15:
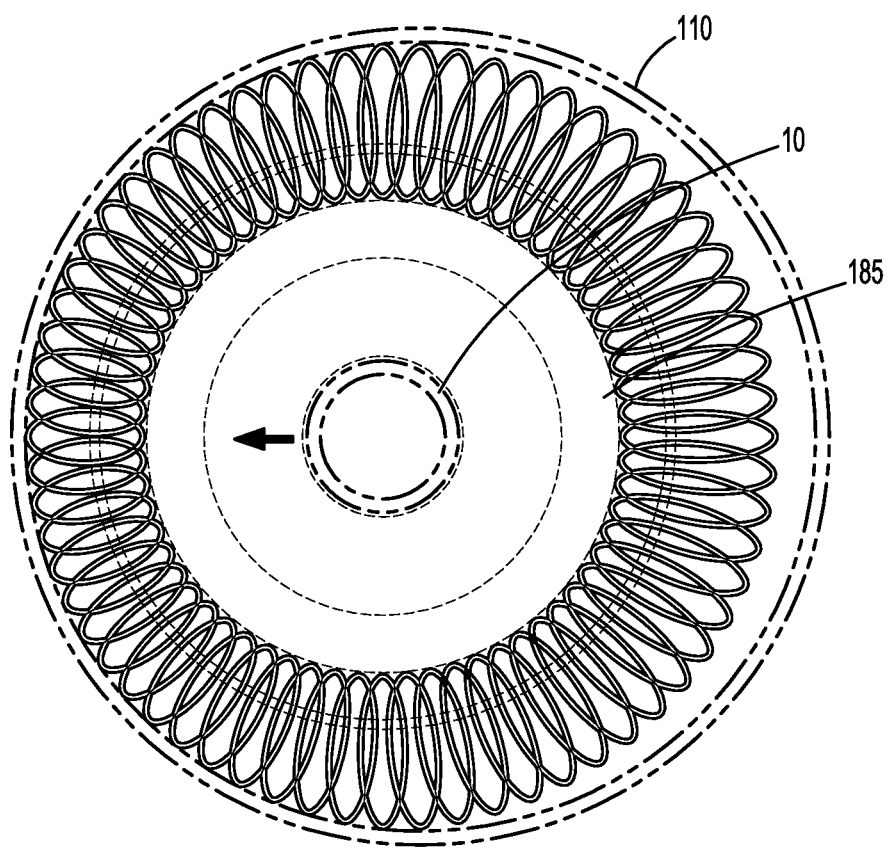
FIG. 15 is a cross-sectional view of the valve housing of FIG. 14, illustrating radial displacement of the valve housing.

With reference to FIGS. 14 and 15, the valve assembly 320 may be radially displaced from a normally biased or a generally centered position such that portions of the centering mechanism 360 are compressed against the lateral wall 110a of the instrument valve housing 110 and portions of the centering mechanism 360 diametrically opposing the compressed portions are disengaged from the lateral wall 110a, as shown in FIG. 15. In the absence of any radial force applied to the surgical instrument, the valve assembly 320 returns to the generally centered position. The use of the centering mechanism 360 is substantially identical to the use of the centering mechanism 160, and thus will not be described herein.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A valve assembly comprising:
   a flange seal member;
   a seal assembly configured to engage a surgical instrument inserted through the seal assembly;
   a centering mechanism including coils, each coil having an inner coil portion and an outer coil portion, the inner coil portions operatively secured to the seal assembly and the outer coil portions configured to engage a surface of a housing of a surgical access device; and a retainer frame assembly configured to couple the centering mechanism, the flange seal member, and the seal assembly as a single construct, the retainer frame assembly including a first member and a second member, the inner coil portions of the centering mechanism disposed between the seal assembly and the second member of the retainer frame assembly.

2. The valve assembly of claim 1, wherein the centering mechanism is formed of a resilient material to transition the centering mechanism between a first state, in which, a central opening of the centering mechanism is disposed in a generally centered position, and a second state, in which, the central opening is radially displaced from the generally centered position.

3. The valve assembly of claim 2, wherein portions of the centering mechanism are compressible when the centering mechanism is in the second state.

4. The valve assembly of claim 1, wherein a gap is defined between adjacent inner coil portions.

5. The valve assembly of claim 4, wherein the first member of the retainer frame assembly includes pins and the second member of the retainer frame assembly defines an annular groove configured to receive the pins.

6. The valve assembly of claim 5, wherein each pin is at least partially disposed in the gap defined between the adjacent inner coil portions such that at least a portion of each inner coil portion is secured between adjacent pins.

7. The valve assembly of claim 1, further including a guard assembly configured to be secured to the flange seal member, the guard assembly configured to protect the seal assembly during insertion and manipulation of a surgical instrument.

8. An access assembly comprising:
a valve housing defining a cavity; and
a valve assembly disposed in the cavity, the valve assembly including:
a flange seal member;
a seal assembly configured to engage a surgical instrument inserted through the seal assembly;
a centering mechanism configured to bias the flange seal member and the seal assembly towards a generally centered position within the cavity, the centering mechanism including coils arranged in a circular configuration, each coil including an outer coil portion configured to engage a lateral surface of the valve housing; and
a retainer frame assembly configured to couple the centering mechanism, the flange seal member, and the seal assembly as a single construct, the retainer frame assembly including a first member and a second member.

9. The access assembly of claim 8, wherein the centering mechanism is formed of a resilient material to transition the centering mechanism between a first state, in which, a central opening of the centering mechanism is disposed in the generally centered position of the cavity, and a second state, in which, the central opening of the centering mechanism is radially displaced from the generally centered position.

10. The access assembly of claim 9, wherein portions of the centering mechanism are compressible when the centering mechanism is in the second state.

11. The access assembly of claim 9, wherein each coil further includes an inner coil portion, and adjacent inner coil portions define a gap between the adjacent inner coil portions.

12. The access assembly of claim 11, wherein the seal assembly includes radial protrusions peripherally arranged about a central opening of the seal assembly, each radial protrusion configured to support a corresponding inner coil portion of the centering mechanism.

13. The access assembly of claim 11, wherein the first member of the retainer frame assembly includes pins and the second member of the retainer frame assembly defines an annular groove configured to receive the pins.

14. The access assembly according to claim 13, wherein each pin of the first member is at least partially disposed in the gap defined between the adjacent inner coil portions such that at least a portion of each inner coil portion is secured between adjacent pins.

15. An access assembly comprising:
a valve housing defining a cavity; and
a valve assembly disposed in the cavity, the valve assembly including:
a flange seal member;
a seal assembly configured to engage a surgical instrument inserted through the seal assembly;
a centering mechanism configured to bias the flange seal member and the seal assembly towards a generally centered position within the cavity, the centering mechanism including a mesh having a toroidal shape, a portion of the mesh configured to engage a lateral surface of the valve housing; and
a retainer frame assembly configured to couple the centering mechanism, the flange seal member, and the seal assembly as a single construct, the retainer frame assembly including a first member and a second member.

16. The access assembly of claim 15, wherein the mesh is disposed distally of an arcuate portion of the flange seal member.

17. The access assembly of claim 15, wherein the mesh defines a central opening and is transitionable between a first state, in which, the central opening of the mesh is in the generally centered position, and a second state, in which, the central opening of the mesh is radially displaced.

18. The access assembly of claim 17, wherein the central opening of the mesh is coaxial with a central opening defined by the seal assembly.

19. The access assembly of claim 16, wherein a portion of the arcuate portion of the flange seal member is in superposed relation with the mesh.

20. The access assembly of claim 16, wherein the mesh is radially compressible such that a portion of the arcuate portion of the flange seal member engages the lateral surface of the valve housing when at least a portion of the mesh is compressed.

* * * * *